United States Patent
Kuno et al.

Patent Number: 6,017,917
Date of Patent: Jan. 25, 2000

[54] GUANIDINE DERIVATIVES

[75] Inventors: Atsushi Kuno; Yoshikazu Inoue, both of Osaka; Kumi Yamasaki, Nishinomiya, all of Japan

[73] Assignee: Fujisawa Pharamceutical Co., Ltd., Osaka, Japan

[21] Appl. No.: 09/091,825

[22] PCT Filed: Dec. 24, 1996

[86] PCT No.: PCT/JP96/03773

§ 371 Date: Jun. 25, 1998

§ 102(e) Date: Jun. 25, 1998

[87] PCT Pub. No.: WO97/25310

PCT Pub. Date: Jul. 17, 1997

[30] Foreign Application Priority Data

Jan. 3, 1996 [GB] United Kingdom ................... 9600063

[51] Int. Cl.⁷ .................................................. A37G 25/30
[52] U.S. Cl. .................. 514/237.8; 514/616; 544/169; 544/382; 548/567; 564/139; 564/156
[58] Field of Search ............................ 544/169; 548/567; 564/139; 514/237.8

[56] References Cited

FOREIGN PATENT DOCUMENTS

PCT/JP94/226709  11/1994  Japan .

Primary Examiner—Robert W. Ramsuer
Attorney, Agent, or Firm—Oblon, Spivak, McClelland, Maier & Neustadt, P.C.

[57] ABSTRACT

Guanidine derivatives of the formula:

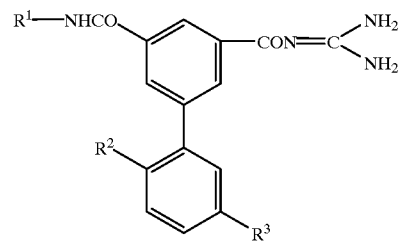

wherein $R^1$ is [di(lower)alkylamino](lower)alkyl, morpholinyl (lower)alkyl, lower alkylpiperazinyl or [lower alkylpyrrolidinyl](lower)alkyl, $R^2$ is halogen, lower alkyl or lower alkoxy, and $R^3$ is halogen, lower alkyl, lower alkoxy or mono(or di or tri)halo(lower)alkyl, and pharmaceutically acceptable salts thereof which are useful as a medicament.

9 Claims, No Drawings

GUANIDINE DERIVATIVES

TECHNICAL FIELD

This invention relates to new guanidine derivatives.

One object of this invention is to provide the new and useful guanidine derivatives and pharmaceutically acceptable salts thereof which possess a strong inhibitory activity on $Na^+/H^+$ exchange in cells.

Another object of this invention is to provide processes for preparation of the guanidine derivatives and salts thereof.

A further object of this invention is to provide a pharmaceutical composition comprising said guanidine derivatives or a pharmaceutically acceptable salt thereof.

Still further object of this invention is to provide a use of said guanidine derivatives or a pharmaceutically acceptable salt thereof as a medicament for the treatment and/or prevention of cardiovascular diseases, cerebrovascular diseases, renal diseases, arteriosclerosis, shock and the like in human being and animals.

BACKGROUND ART

Some guanidine derivatives having pharmaceutical activities such as inhibitory activity on $Na^+/H^+$ exchange in cells have been known as described in WO 94/26709.

DISCLOSURE OF INVENTION

The object guanidine derivatives of the present invention are novel and can be represented by the following general formula (I):

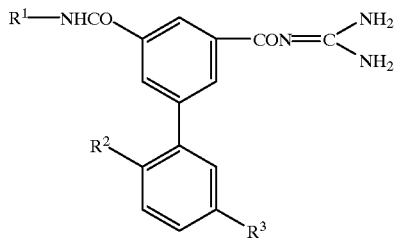

wherein $R^1$ is [di(lower)alkylamino](lower)alkyl, morpholinyl (lower)alkyl, lower alkylpinerazinyl or [lower alkylpyrrolidinyl](lower)alkyl, $R^2$ is halogen, lower alkyl or lower alkoxy, and $R^3$ is halogen, lower alkyl, lower alkoxy or mono(or di or tri)halo(lower)alkyl.

The object compound (I) of the present invention can be prepared by the following process.

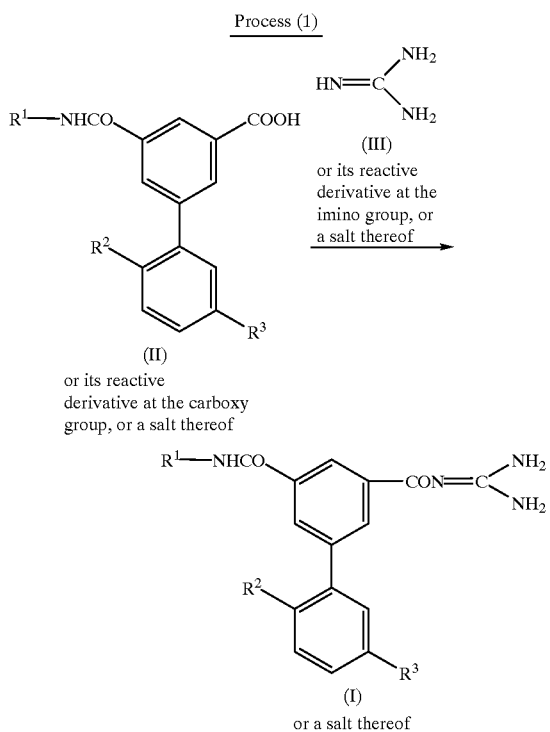

wherein $R^1$, $R^2$ and $R^3$ are each as defined above.

The starting compound can be prepared by the following processes or Preparations mentioned below, or similar manners thereto.

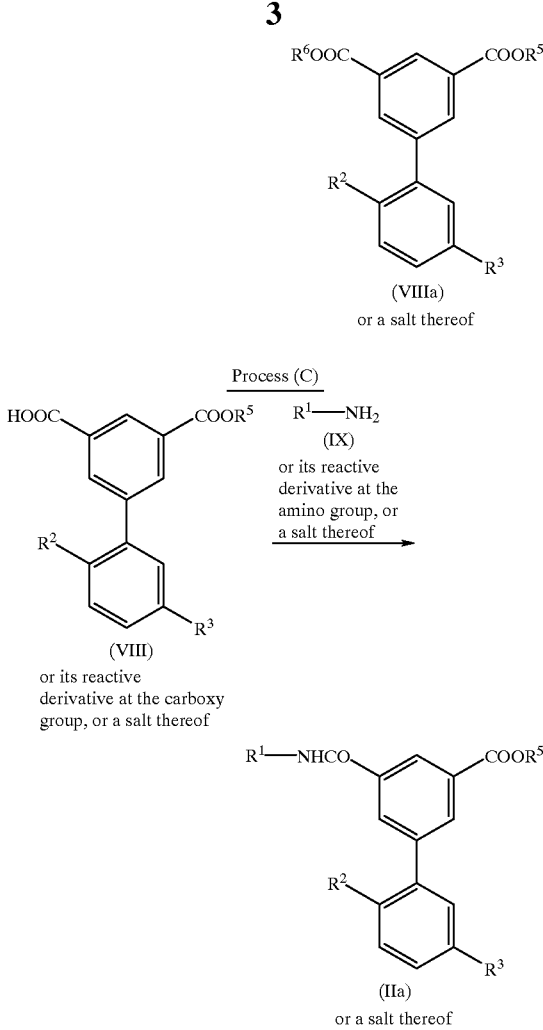

wherein
R¹, R² and R³ are each as defined above,
R⁴ is lower alkyl,
R⁵ and R⁶ are each hydrogen or lower alkyl, and
X¹ and X² are each a leaving group.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, fumarate, citrate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl moiety" in the terms "[di(lower)alkylamino](lower)alkyl", "morpholinyl (lower)alkyl", "lower alkylpiperazinyl", "[lower alkylpyrrolidinyl](lower)alkyl", "mono(or di or tri)halo (lower)alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, and in which more preferable example may be $C_1$–$C_4$ alkyl.

Suitable "lower alkoxy" may include methoxy, ethoxy, propoxy, isopropoxy, butoxy, isobutoxy, tert-butoxy, pentyloxy, tert-pentyloxy, hexyloxy and the like.

Suitable "halogen" and "halogen moiety" in the term "mono(or di or tri)halo(lower)alkyl" may include fluorine, bromine, chlorine and iodine.

Suitable "leaving group" may include acid residue, lower alkoxy as exemplified above, and the like.

Suitable "acid residue" may include halogen as exemplified above, acyloxy, and the like.

Suitable "acyl moiety" in the term "acyloxy" may include Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g., methoxycarbonyl, ethoxycarbonyl, tert-butoxycarbonyl, tert-pentyloxycarbonyl, heptyloxycarbonyl, etc.); lower or higher alkylsulfonyl (e.g., methylsulfonyl, ethylsulfonyl, etc.); mono(or di or tri)halo(lower)alkylsulfonyl (e.g., trifluoromethylsulfonyl, trichloromethylsulfonyl, etc.); lower or higher alkoxysulfonyl (e.g., methoxysulfonyl, ethoxysulfonyl, etc.); cyclo(lower)alkylcarbonyl (e.g., cyclopentylcarbonyl, cyclohexylcarbonyl, etc.); or the like;

Aromatic acyl such as aroyl (e.g., benzoyl, toluoyl, naphthoyl, etc.); ar(lower)alkanoyl [e.g., phenyl(lower) alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.]; ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower) alkenoyl (e.g., naphthylpropenoyl, naphthylbutenoyl, etc.), etc.]; ar(lower)alkoxycarbonyl [e.g., phenyl(lower) alkoxycarbonyl (e.g., benzyloxycarbonyl, etc.), etc.]; aryloxycarbonyl (e.g., phenoxycarbonyl, naphthyloxycarbonyl, etc.); aryloxy(lower)alkanoyl (e.g., phenoxyacetyl, phenoxypropionyl, etc.); arylglyoxyloyl (e.g., phenylglyoxyloyl, naphthylglyoxyloyl, etc.); arylsulfonyl (e.g., phenylsulfonyl, p-tolylsulfonyl, etc.); or the like.

Suitable "[di(lower)alkylamino](lower)alkyl" may include [dimethylamino]methyl, 1-(or 2-)[dimethylamino] ethyl, 1-(or 2- or 3-)[(dimethylamino]propyl, [diethylamino] methyl, 1-(or 2-)[diethylaminolethyl, 1-(or 2- or 3-) [diethylamino]-propyl, and the like.

Suitable "[lower alkylpyrrolidinyl](lower)alkyl" may include [1-(or 2- or 3- or 4- or 5-)methyl-1-(or 2- or 3-)-pyrrolidinyl]methyl, 1-(or 2-)[1-(or 2- or 3- or 4- or 5-)methyl-1-(or 2- or 3-)pyrrolidinyl]ethyl, 1-(or 2- or 3-)-[1-(or 2- or 3- or 4- or 5-)methyl-1-(or 2- or 3-)-pyrrolidinyl] propyl, [1-(or 2- or 3- or 4- or 5-)ethyl-1-(or 2- or 3-)pyrrolidinyl]methyl, 1-(or 2-)[1-(or 2- or 3- or 4- or 5-)ethyl-1-(or 2- or 3-)pyrrolidinyl]ethyl, 1-(or 2- or 3-)[1-(or 2- or 3- or 4- or 5-)ethyl-1-(or 2- or 3-)-pyrrolidinyl] propyl, and the like.

Suitable "mono(or di or tri)halo(lower)alkyl" may include fluoromethyl, chloromethyl, bromomethyl, difluoromethyl, dichloromethyl, dibromomethyl, trifluoromethyl, trichloromethyl, tribromomethyl, 1-(or 2-)fluoroethyl, 1-(or 2-)chloroethyl, 1-(or 2-)-bromoethyl, and the like.

Preferred embodiments of the object compound (I) are as follows:

$R^1$ is [di (lower)alkylamino](lower)alkyl (more preferably [di(Cl-$C_4$ alkyl)amino]($C_1$–$C_4$)alkyl, much more preferably 2-(dimethylamino)ethyl, 3-(dimethylamino) propyl, 2-(di-ethylamino)ethyl or 3-(diethylamino) propyl, most preferably 2-(dimethylamino)ethyl or 2-(diethylamino)ethyl], morpholinyl(lower)alkyl [more preferably morpholinyl-($C_1$–$C_4$)alkyl, much more preferably 2-morpholinoethyl or 3-morpholinopropyl, most preferably 2-norpholinoethyl], or [lower alkylpyrrolidinyl](lower) alkyl [more preferably [$C_1$–$C_4$ alkylpyrrolidinyl] ($C_1$–$C_4$)alkyl, most preferably 2-(1-methylpyrrolidin-2-yl)ethyl], $R^2$ is halogen (more preferably fluorine or chlorine, most preferably chlorine), lower alkyl (more preferably $C_1$–$C_4$ alkyl, most preferably methyl), or lower alkoxy (more preferably $C_1$–$C_4$ alkoxy, most preferably methoxy, and $R^3$ is halogen (more preferably fluorine or chlorine, most preferably chlorine), lower alkyl (more preferably $C_1$–$C_4$ alkyl, most preferably methyl), lower alkoxy (more preferably $C_1$–$C_4$ alkoxy, most preferably methoxy), or mono(or di or tri)halo(lower)alkyl [more preferably mono(or di or tri)halo(Cl-$C_4$)alkyl, much more preferably trihalo($C_1$–$C_4$)alkyl, most preferably trifluoromethyl].

More preferred embodiments of the object compound (I) are as follows $R^1$ is [di(lower)alkylamino](lower)alkyl (more preferably [di($C_1$–$C_4$ alkyl)amino]($C_1$–$C_4$)alkyl, most preferably 2-(dimethylamino)ethyl or 2-(diethylamino)ethyl]), $R^2$ is halogen (more preferably chlorine), and $R^3$ is halogen (more preferably chlorine).

The processes for preparing the object and starting compounds of the present invention are explained in detail in the following.

Process (1)

The compound (I) or a salt thereof can be prepared by reacting the compound (II) or its reactive derivative at the carboxy group, or a salt thereof with the compound (III) or its reactive derivative at the imino group, or a salt thereof.

Suitable reactive derivative at the imino group of the compound (III) may include a silyl derivative formed by the reaction of the compound (III) with a silyl compound such as bis(trimethylsilyl)acetamide, mono(trimethylsilyl) acetamide [e.g. N-(trimethylsilyl)acetamide], bis (trimethylsilyl)urea or the like; a derivative formed by the reaction of the compound (III) with phosphorus trichloride or phosgene, and the like.

Suitable reactive derivative at the carboxy group of the compound (II) may include a conventional one such as an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 1-hydroxy-1H-benzotriazole, 4-substituted imidazole, dimethylpyrazole, triazole or tetrazole; or an activated ester [e.g. cyanomethyl ester, methyl ester, ethyl ester, methoxymethyl ester, dimethyliminomethyl [$(CH_3)_2\overset{+}{N}$=CH—]ester, vinyl ester, propargyl ester, 2-trifluoromethylsulfonylaminoethyl ester, 2-trifluoromethylsulfonylaminopropyl ester, 2-methyl-2-trifluoromethylsulfonylaminopropyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, benzothiazolyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylinidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxyberzisoxazolium salt; 2-ethyl-5-(m-sulfophenyl) isoxazolium hydroxide intramolecular salt; 1-(p-chlorobenzenesulfonyloxy)-6-chloro-1H-benzotriazole; a combination of N-lower alkylhalopyridinium halide (e.g., 1-methyl-2-chloropyridinium iodide, etc.) and tri(lower) alkylamine (e.g. triethylamine, etc.); so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower) alkylbenzylamine, alkali metal lower alkoxide (e.g. sodium methoxide, etc.) or the like.

The reaction temperature is not critical, and the reaction is usually carried out under cooling to warming.

Process (A)

The compound (VI) can be prepared by reacting the compound (IV) or a salt thereof with the compound (V) and then by subjecting the resultant compound to elimination reaction of lower alkyl.

The reaction can be carried out in the manners disclosed in Preparation 1 or similar manners thereto.

Process (B) The compound (VIIa) or a salt thereof can be prepared by reacting the compound (VII) or a salt thereof with the compound (VI).

The reaction can be carried out in the manner disclosed in Preparation 4 or similar manners thereto.

Process (C)

The compound (IIa) or a salt thereof can be prepared by reacting the compound (VIII) or its reactive derivative at the carboxy group, or a salt thereof with the compound (IX) or its reactive derivative at the amino group, or a salt thereof.

This reaction can be carried out in a similar manner to that of the aforementioned Process (1), and therefore the reagents to be used and the reaction conditions (e.g., solvent, reaction temperature, etc.) can be referred to those of the Process (1).

It is to be noted that the object compound (I) may include one or more stereoisomer(s) due to asymmetric carbon atom(s) and double bond(s) and all such isomers and mixture thereof are included within the scope of this invention.

It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

Regarding the object compound (I), it is to be understood that they include tautomeric isomers.

That is, a group of the formula:

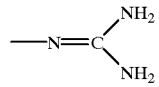

can be also alternatively represented by its tautomeric formula:

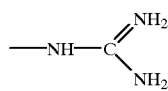

That is, both of the said groups are in the state of equilibrium and such tautomerism can be represented by that following equilibrium:

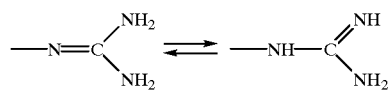

And it is obvious to any person skilled in the arts that both of the tautomeric isomers are easily convertible reciprocally and are included within the same category of the compound per se.

Accordingly, both of the tautomeric forms of the object compound (I) are clearly included within the scope of the present invention.

In the present specification, the object compound including the group of such tautomeric isomers is represented by using one of the expressions therefor, that is the formula:

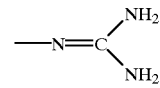

only for the convenient sake.

Suitable salts of the object and starting compounds and their reactive derivatives in Processes (1) and (A)~(C) can be referred to the ones as exemplified for the compound (I).

The new guanidine derivatives (I) and a pharmaceutically acceptable salt thereof of the present invention possess a strong inhibitory activity on $Na^+/H^+$ exchange in cells and therefore are useful as an inhibitor on $Na^+/H^+$ exchange in cells.

Accordingly, the new guanidine derivatives (I) and a pharmaceutically acceptable salt thereof can be used for the expectorant and for the treatment and/or prevention of cardiovascular diseases [e.g. hypertension, angina pectoris, myocardial infarction, heart failure (e.g. congestive heart failure, acute heart failure, cardiac hypertrophy, etc.), arrhythmia (e.g. ischenic arrhythmia, arrhythmia due to myocardial infarction, arrhythmia after PTCA or after thrombolysis, etc.), restenosis after PTCA, etc.], cerebrovascular diseases [e.g. ischemic stroke, hemorrhagic stroke, etc.], renal diseases [e.g. diabetic nephropathy, ischemic acute renal failure, etc.], arteriosclerosis, shock [e.g. hemorrhagic shock, endotoxin shock, etc.] and the like, and can also be used as an agent for ischemic reperfusion injury, myocardial protection, organ protection in organ transplantation, open heart surgery, and the like.

In order to show the utilities of the guanidine derivatives (I) and a pharmaceutically acceptable salt thereof of the present invention, pharmacological test data of the representative compound of the guanidine derivatives (I) are illustrated in the following.

[1] Test Compound (a) [5-(2,5-dichlorophenyl)-3-[(2-morpholinoethyl)-carbamoyl]benzoyl]guanidine.dihydrochloride

[2] Inhibitory activity on $Na^+/H^+$ exchange in cells

[i] Test Method

Procedure was carried out according to a similar manner to the method described in Enzymology 173, 777 (1989).

Cell Preparation

One male SD strain rat weighing 250–300 g was sacrificed with the blow on the head. Then, the thymus was removed into ice-cold NaCl medium (140 mM sodium chloride, 1 mM potassium chloride, 1 mM calcium chloride, 1 mM magnesium chloride, 10 mM glucose and 20 mM N-2-hydroxyethylpiperazine-N'-2-ethanesulfonic acid (HEADS)—pH 7.3), cut in small fragments, and transferred to glass homogenizer. The cells were dissociated by gentle strokes, and the resulting suspension was filtrated through six layers of surgical gauze and the filtrate was centrifuged at 4° C. at 1000 g for 5 minutes. The pellet was resuspended in RPMI 1640 medium (pH 7.3) at room temperature to adjust final cell concentration ($1\times10^7$ cells/ml).

Assay

This method detects the swelling that accompanies activation of $Na^+/H^+$ exchanger in cells incubated with sodium propionate. Propionic acid rapidly penetrates through the membrane. Intracellular dissociation brings about cytoplasmic acidification and consequently activation of $Na^+/H^+$ exchanger, which exchange extracellular $Na^+$ for cytoplasmic H⁺. The uptake of osmotically obliged water was manifested as cell swelling.

Cell sizing and counting were performed electrically with the Coulter Counter-Channelyzer (AT-II). 0.1 ml Thymocytes solution were suspended in 20 ml sodium-propionate medium (140 mM sodium propionate, 1 mM potassium chloride, 1 mM calcium chloride, 1 mM magnesium chloride, 10 mM glucose, 20 mM N-2-hydroxyethylpiperazine-N'-2-ethanesulfonic acid (HEPES)—pH 6.8) including test compound solved in dimethyl sulfoxide (final concentration of dimethyl sulfoxide was 0.1%). During 4 minutes, increase of cell volume induced by Na⁺/H⁺ exchanger was kept linear, and the time course of swelling was observed each minute after the addition of thymocytes. Rate of Swelling (Δ volume/min.) was measured by using 3–5 concentrations of test compound. Then, apparent Ki value of test compound was calculated by using Line weaver-Burk plot.

[3] Test Result:

| Test Compound | Ki (M) |
|---|---|
| (a) | <1.0 × 10⁻⁷ |

The object compound (I) or its pharmaceutically acceptable salts can usually be administered to mammals including human being in the form of a conventional pharmaceutical composition such as oral dosage form (e.g., capsule, microcapsule, tablet, granule, powder, troche, syrup, aerosol, inhalation, suspension, emulsion, etc.), injection dosage form, suppository, ointment, or the like.

The pharmaceutical composition of this invention can contain various organic or inorganic carrier materials, which are conventionally used for pharmaceutical purpose such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyleneglycol, sucrose, starch, etc.), disintegrator (,e.g., starch, carboxymethyl cellulose, calcium salt of carboxymethyl cellulose, hydroxypropylstarch, sodium glycolestarch, sodium bicarbonate, calcium phosphate, calcium citrate, etc.), lubricant (e.g., magnesium stearate, talc, sodium laurylsulfate, etc.), flavoring agent (e.g., citric acid, mentol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water, etc.), base wax (e.g., cacao butter, polyethyleneglycol, white petrolatum, etc.).

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following Preparations and Examples are given for the purpose of illustrating the present invention in more detail.

Preparation 1

To a cold (−78° C.) solution of 2,5-dichloroiodobenzene (50 g) and triisopropoxyborane (46.5 ml) in tetrahydrofuran (500 ml) was added dropwise n-butyllithium in hexane (1.69 M, 119 ml). The mixture was stirred at −78° C. for 30 minutes. The reaction mixture was poured into 2M hydrochloric acid solution (180 ml) and stirred for 10 minutes. The product was extracted with ether (200 ml) 2 times, and the organic layers were combined, washed with brine, dried over magnesium sulfate and evaporated in vacuo. To the residue was added n-hexane (60 ml) and the crystalline was collected, washed with n-hexane and dried to give 2,5-dichlorophenyl-dihydroxyborane (21.0 g).

mp: 219–220° C.

IR (Nujol): 1580, 1155, 1000, 820 cm⁻¹

NMR (DMSO-d₆, δ): 7.3–7.5 (3H, m)

Preparation 2

The following compounds were obtained according to a similar manner to that of Preparation 1.

(1) 2,5-Dimethoxyphenyl-dihydroxyborane mp: 96–98° C.

IR (Nujol): 1610, 1585, 1570, 1215, 730 cm⁻¹

NMR (DMSO-d₆, δ): 3.70 (3H, s), 3.77 (3H, s), 6.88–6.99 (2H, m), 7.12–7.14 (1H, m), 7.75 (2H, s)

(2) 2,5-Difluorophenyl-dihydroxyborane mp: 239–241° C.

IR (Nujol): 3300 (br), 1620, 1120 cm⁻¹

NMR (DMSO-d₆, δ): 7.08–7.33 (3H, m), 8.30 (2H, br s)

(3) 5-Chloro-2-methylphenyl-dihydroxyborane mp: 184–186° C.

IR (Nujol): 1590, 1400, 1340 cm⁻¹

NMR (DMSO-d₆, δ): 2.62 (3H, s), 7.19 (1H, d, J=8.2 Hz), 7.30 (1H, dd, J=8.2, 2.4 Hz), 7.79 (1H, d, J=2.4 Hz)

(4) 2-Chloro-5-methylphenyl-dihydroxyborane mp: 101–103° C.

IR (Nujol): 3270, 1730, 1630, 1590, 1340 cm⁻¹

NMR (DMSO-d₆, δ): 2.26 (3H., s), 7.13 (1H, dd, J=8.0, 1.9 Hz), 7.20 (1H, d, J=1.9 Hz), 7.22 (1H, d, J=8.0 Hz), 8.26 (2H, s)

(5) 2-Chloro-5-trifluoromethylphenyl-dihydroxyborane mp: 175–177° C.

IR (Nujol): 3350, 1600, 1580, 1320 cm⁻¹

NMR (DMSO-d₆, δ): 7.61 (1H, d, J=8.2 Hz), 7.68–7.74 (2H, s)

(6) 5-Chloro-2-methoxyphenyl-dihydroxyborane mp: 145–147° C.

IR (Nujol): 3400, 1590, 1570, 1230 cm⁻¹

NMR (DMSO-d₆, δ): 3.79 (3H, s), 7.00 (1H, d, J=8.7 Hz), 7.38 (1H, d, J=2.8 Hz), 7.44 (1H, d, J=8.7, 2.8 Hz), 7.87 (2H, s)

Preparation 3

To a mixture of 2-chloro-5-methoxyphenol (3.0 g), 2,6-lutidine (2.64 ml) and 4-dimethylaminopyridine (0.356 g) in 1,2-dichloroethane (60 ml) was added dropwise bis (trifluoromethanesulfonic)anhydride (3.82 ml) at −30° C. over 10 minutes. The mixture was stirred at −30° C. for 30 minutes and then was warmed to room temperature. After 2 hours, water was added to the reaction mixture and two layers were separated. The organic layer was dried over magnesium sulfate and evaporated in vacuo. The residue was dissolved in ethyl acetate (60 ml) and was washed successively with 10% hydrochloric acid solution, water, sodium hydrogencarbonate solution and brine. The organic layer was dried over magnesium sulfate and evaporated in vacuo to give 2-chloro-5-methoxy-1-trifluoromethylsulfonyloxybenzene (4.99 g, 90.8%).

IR (Neat): 1600, 1580, 1490, 1220, 1140 cm⁻¹

NMR (DMSO-d₆, δ): 3.83 (3H, s), 7.14 (1H, dd, J=8.9, 2.9 Hz), 7.20 (1H, d, J=2.9 Hz), 7.68 (1H, d, J=8.9 Hz)

Preparation 4

The mixture of 2,5-dichlorophenyl-dihydroxyborane (9.35 g), 5-methoxycarbonyl-3-iodobenzoic acid (10 g), potassium carbonate (14.0 g) and palladium(II) acetate (0.073 g) in water (200 ml) was stirred at 40° C. for four hours. Undissolved material was filtered, washed with water (100 ml), suspended in water (150 ml) and adjusted to pH 2.0 with 6N hydrochloric acid. The mixture was extracted two times with a mixture of ethyl acetate (120 ml) and tetrahydrofuran (60 ml), washed with brine, dried over magnesium sulfate and evaporated in vacuo. The residual crystalline was washed with n-hexane to give 3-methoxycarbonyl-5-(2,5-dichlorophenyl)benzoic acid (5.36 g, 50.4%).

mp: 222–224° C.

IR (Nujol): 1730, 1710, 1600, 1140, 1100, 1040 cm$^{-1}$

NMR (DMSO-d$_6$, δ): 3.92 (3H, s), 7.5–7.7 (3H, m), 8.22 (2H, S), 8.53 (1H, s), 13.53 (1H, s)

(+) APCI MASS: 325 [M+H]$^+$, 327 [M+H]$^+$

Preparation 5

The following compound was obtained according to a similar manner to that of Preparation 4.

5-(2,5-Dimethoxyphenyl)-3-methoxycarbonylbenzoic acid mp: 212–214° C.

IR (Nujol): 1730, 1690, 1500, 1265, 1040, 720 cm$^{-1}$

NMR (DMSO-d$_6$, δ): 3.73 (3H, s), 3.77 (3H, s), 3.91 (3H, s), 6.95 (1H, d, J=3.0 Hz), 6.99 (1H, dd, J=8.7 Hz, 3.0 Hz), 7.10 (1H, d, J=8.7 Hz), 8.22–8.27 (2H, m), 8.43–8.46 (1H, m), 13.40 (1H, br)

(+) APCI MASS: 317 [M+H]$^+$

Preparation 6

A mixture of methyl 3-((2-dimethylaminoethyl) carbamoyl]-5-(trifluoromethylsulfonyloxy)benzoate (2 g), 2,5-dichlorophenyl-dihydroxyborane 1.25 g), tetrakis (triphenylphosphine)palladium(0) (0.17 g) and triethylamine (1.52 g) in N,N-dimethylformamide (40 ml) was heated at 100° C. for 3 hours under nitrogen atmosphere. After evaporating the solvent, the residue was dissolved in a mixture of ethyl acetate (100 ml) and water (100 ml). The organic layer was successively washed with 10% potassium carbonate aqueous solution, brine and dried over magnesium sulfate. The solvent was evaporated in vacuo and the residue was purified by column chromatography on silica gel (100 ml) eluting with a mixture of chloroform and methanol (20:1). The fractions containing the desired products were collected and evaporated in vacuo. The residue was crystallized from diisopropyl ether to afford methyl 5-(2,5-dichlorophenyl)-3-[(2-dimethylaminoethyl)carbamoyl] benzoate.

mp: 104–105° C.

IR (Nujol): 3250, 1730, 1640, 1160, 730 cm$^{-1}$

NMR (DMSO-d$_6$, δ): 2.18 (6H, s), 2.42 (2H, t, J=6.8 Hz), 3.40 (2H, dt, J=6.8, 5.5 Hz), 3.92 (3H, s), 7.55 (1H, dd, J=8.4, 2.6 Hz), 7.64 (1H, d, J=2.6 Hz), 7.66 (1H, d, J=8.4 Hz), 8.14 (1H, dd, J=1.6, 1.6 Hz), 8.18 (1H, dd, J=1.6, 1.6 Hz), 8.50 (1H, dd, J=1.6, 1.6 Hz), 8.70 (1H, t, J=5.5 Hz)

(+) APCI MASS: 395 [M+H]$^+$, 397 [M+H]$^+$

Preparation 7

The following compounds were obtained according to a similar manner to that of Preparation 6.

(1) Methyl 5-(2,5-difluorophenyl)-3-[(2-dimethylaminoethyl) carbamoyl]benzoate.hydrochloride mp: 164–165° C.

IR (Nujol): 3300, 1730, 1660, 1530, 1260 cm$^{-1}$

NMR (DMSO-d$_6$, δ): 2.83 (6H, s), 3.28–3.38 (2H, m), 3.67–3.79 (2H, m), 3.93 (3H, s), 7.31–7.52 (2H, m), 7.64–7.74 (1H, m), 8.29 (1H, s), 8.43 (1H, s), 3.51 (1H, s), 9.26 (1H, t, J=5.3 Hz), 10.45 (1H, br s)

(+) APCI MASS: 363 [M+H]$^+$ (2) Methyl 5-(5-chloro-2-methylphenyl)-3-[(2-dimethylaminoethyl) carbamoyl]benzoate.hydrochloride mp: 170–173° C.

IR (Nujol): 1730, 1640, 1540, 1260 cm$^{-1}$

NMR (DMSO-d$_6$, δ): 2.21 (3H, s), 2.82 (6H, s), 3.25–3.37 (2H, m), 3.65–3.75 (2H, m), 3.91 (3H, s), 7.37–7.45 (3H, m), 8.04 (1H, dd, J=1.5, 1.5 Hz), 8.18 (1H, dd, J=1.5, 1.5 Hz), 8.50 (1H, dd, J=1.5, 1.5 Hz), 9.13 (1H, J=5.3 Hz), 10.25 (1H, br s)

(+) APCI MASS: 375 [M+H]$^+$, 377 [M+H]$^+$ (3) Methyl 5-(2-chloro-5-methylphenyl)-3-[(2-dimethylaminoethyl)carbamoyl]benzoate.hydrochloride mp: 135–137° C.

IR (Nujol): 3250, 1720, 1660, 1530, 1270 cm$^{-1}$

NMR (DMSO-d$_6$, δ): 2.37 (3H, s), 2.82 (6H, s), 3.25–3.37 (2H, m), 3.64–3.77 (2H, m), 3.92 (3H, s), 7.29 (1H, dd, J=8.1, 1.7 Hz), 7.39 (1H, d, J=1.7 Hz), 7.50 (1H, d, J=8.1 Hz), 8.15 (1H, dd, J=1.6, 1.6 Hz), 8.26 (1H, dd, J=1.6, 1.6 Hz), 8.52 (1H, dd, J=1.6, 1.6 Hz), 9.14 (1H, t, J=5.5 Hz), 10.41 (1H, br s)

(+) APCI MASS: 375 [M+H]$^+$, 377 [M+H]$^+$ (4) Methyl 5-(2-chloro-5-trifluoromethylphenyl)-3-[(2-dimethylaminoethyl)carbamoyl]benzoate.hydrochloride mp: 190–192° C.

IR (Nujol): 1730, 1650, 1540, 1260 cm$^{-1}$

NMR (DMSO-d$_6$, δ): 2.82 (6H, s), 3.25–3.37 (2H, m), 3.64–3.78 (2H, m), 3.92 (3H, s), 7.85–7.95 (3H, m), 8.21 (1H, dd, J=1.6, 1.6 Hz), 8.32 (1H, dd, J=1.6, 1.6 Hz), 8.56 (1H, dd, J=1.6, 1.6 Hz), 9.21 (1H, t, J=5.4 Hz), 10.49 (1H, br s)

(+) APCI MASS: 429 [M+H]$^+$, 431 [M+H]$^+$ (5) Methyl 5-(5-chloro-2-nethoxyphenyl) -3-(2-dimethylaminoethyl)carbamoyl] benzoate.hydrochloride mp: 196–198° C.

IR (Nujol): 3250, 1720, 1650, 1520, 1250 cm$^{-1}$

NMR (DMSO-d$_6$, δ): 2.82 (6H, s), 3.25–3.35 (2H, m), 3.65–3.75 (2H, m), 3.80 (3H, s), 3.91 (3H, s), 7.20 (1H, d, J=8.6 Hz), 7.47 (1H, dd, J=8.6, 2.6 Hz), 7.51 (1H, d, J=2.6 Hz), 8.22 (1H, dd, J=1.6, 1.6 Hz), 8.28 (1H, dd, J=1.6, 1.6 Hz), 8.46 (1H, dd, J=1.6, 1.6 Hz), 9.13 (1H, J=5.4 Hz), 10.43 (1H, br s)

(+) APCI MASS: 391 [M+H]$^+$, 393 [M+H]$^+$ (6) Methyl 5-(2,5-dimethylphenyl)-3-[(2-dimethylaminoethyl)carbamoyl]benzoate IR (Film): 3250, 1720, 1035 cm$^{-1}$ NMR (DMSO-d$_6$, δ): 2.19 (6H, s), 2.44 (2H, t, J=6.8 Hz), 3.3–3.5 (2H, m), 3.91 (3H, s), 7.05–7.25 (3H, m), 7.98 (1H, s), 8.09 (1H, s), 8.45 (1H, s), 8.72 (1H, t, J=5.4 Hz)

Preparation 8

A mixture of 2-chloro-5-methoxy-1-trifluoromethyl-sulfonyloxybenzene (0.30 g), 3,5-dimethoxycarbonylphenyl-dihydroxyborane (0.32 g), triethylamine (0.43 ml) and tetrakis(triphenylphosphine) palladium(0) (0.036 g) in N,N-dimethylformamide (6 ml) was heated at 100° C. for 3 hours under nitrogen atmosphere. The reaction mixture was poured into water (30 ml) and the product was extracted with ethyl acetate (30 ml). The organic layer was successively washed with water, potassium carbonate solution, hydrochloric acid solution and brine, and was dried over magnesium sulfate. The solvent was removed under reduced pressure. The residue was triturated with diethyl ether and the product was collected by filtration, washed with diethyl ether to afford dimethyl 5-(2-chloro-5-methoxyphenyl)isophthalate.

mp: 152–154° C.

IR (Nujol): 1720, 1590, 1300, 1240 cm$^{-1}$

NMR (DMSO-d$_6$, δ): 3.81 (3H, s), 3.92 (6H, s), 7.02–7.10 (2H, m), 7.49–7.54 (1H, m), 8.22 (2H, d, J=1.6 Hz), 8.51 (1H, dd, J=1.6, 1.6 Hz)

(+) APCI MASS: 335 [M+H]+, 337 [M+H]$^+$

Preparation 9

A mixture of dimethyl 5-(2-chloro-5-methoxyphenyl)-isophthalate (1.20 g) and potassium hydroxide (0.23 g) in methanol (60 ml) and 1,4-dioxane (20 ml) was refluxed for 48 hours. The mixture was evaporated in vacuo and to the residue was added ethyl acetate and water. Two layers were separated and the aqueous layer was acidified with hydrochloric acid solution. The product was extracted with ethyl acetate and the organic layer was washed with water and brine, dried over magnesium sulfate and evaporated in vacuo to give 5-(2-chloro-5-methoxyphenyl)-3-methoxycarbonylbenzoic acid (0.96 g, 83.5%).

mp: 214–216° C.

IR (Nujol): 1720, 1690, 1590, 1220 cm$^{-1}$

NMR (DMSO-d$_6$, δ): 3.82 (3H, s), 3.92 (1H, s), 7.02–7.07 (2H, m), 7.52 (1H, d, J=9.2 Hz), 8.18 (1H, dd, J=1.6, 1.6 Hz), 8.21 (1H, dd, J=1.6, 1.6 Hz), 8.51 (1H, dd, J=1.6, 1.6 Hz), 13.45 (1H, br s)

(+) APCI MASS: 321 [M+H]$^+$

Preparation 10

To a mixture of 3-methoxycarbonyl-5-(2,5-dichlorophenyl)benzoic acid (1.0 g), N,N-dimethylethylenediamine (0.223 g) and 1-hydroxybenzotriazole (0.376 g) in N,N-dimethylformamide (10 ml) was added 1-ethyl-3-(3-dimethylaminopropyl)carbodiimide (0.533 g) under ice cooling, and then the solution was stirred for five hours at room temperature. After evaporating the solvent, the residue was dissolved in a mixture of ethyl acetate (50 ml) and water (50 ml) and adjusted to pH 10 with 6N aqueous potassium carbonate solution with stirring. The organic layer was washed with brine, dried over magnesium sulfate and evaporated in vacuo. The residue was purified by column chromatography on silica gel (100 ml) eluting with a mixture of chloroform and methanol (20:1). The fractions containing the desired product were collected and evaporated in vacuo. The residue was dissolved in ethanol (8 ml) and added slightly excess 4N hydrogen chloride in dioxane to afford methyl 5-(2,5-dichlorophenyl)-3-[(2-dimethylaminoethyl) carbamoyl)benzoate.hydrochloride (0.43 g).

mp: 213–216° C.

IR (Nujol): 1730, 1655, 1520, 1260, 1235, 1095 cm$^{-1}$

NMR (DMSO-d$_6$, δ): 2.82 (6H, s), 3.29 (2H, t, J=5.7 Hz), 3.69 (2H, t, d, J=5.7 Hz, 5.2 Hz), 3.92 (3H, s), 7.56 (1H, dd, J=8.6, 2.3 Hz), 7.66 (1H, d, J=8.6 Hz), 7.68 (1H, d, J=2.3 Hz), 8.18 (1H, s), 8.29 (1H, s), 8.54 (1H, s), 9.20 (1H, t, J=5.2 Hz), 10.52 (1H, s)

(+) APCI MASS: 395 [M+H]$^+$, 397 [M+H]$^+$

Preparation 11

The following compounds were obtained according to a similar manner to that of Preparation 10.

(1) Methyl 5-(2,5-dichlorophenyl)-3-(4-methylpiperazin-1-ylcarbamoyl)benzoate mp: 220–222° C. (dec.)

IR (Nujol): 3200, 1720, 1640, 1330, 1230 cm$^{-1}$

NMR (DMSO-d$_6$, δ): 2.19 (3H, s), 2.35–2.50 (4H, m), 2.89 (4H, t, J=4.6 Hz), 3.91 (3H, s), 7.56 (1H, dd, J=8.8, 2.2 Hz), 7.65 (1H, d, J=2.2 Hz), 7.67 (1H, d, J=8.8 Hz), 8.10 (1H, dd, J=1.6, 1.6 Hz), 8.13 (1H, dd, J=1.6, 1.6 Hz), 8.42 (1H, dd, J=1.6, 1.6 Hz), 9.69 (1H, s)

(+) APCI MASS: 422 [M+H]$^+$, 424 [M+H]$^+$ (2) Methyl 5-(2,5-dichlorophenyl)-3-[(2-diethylaminoethyl)-carbamoyl]benzoate IR (Neat): 3300, 1720, 1650, 1540, 1260 cm$^{-1}$ NMR (DMSO-d$_6$, δ): 0.97 (6H, t, J=7.1 Hz), 2.45–2.65 (6H, m), 3.30–3.42 (2H, m), 3.92 (3H, s), 7.56 (1H, dd, J=8.5, 2.6 Hz), 7.65 (1H, d, J=2.6 Hz), 7.67 (1H, d, J=8.5 Hz), 8.14 (1H, dd, J=1.6, 1.0 Hz), 8.17 (1H, dd, J=1.6, 1.6 Hz), 8.49 (1H, dd, J=1.6, 1.6Hz), 8.71 (1H, t, J=5.5 Hz)

(+) APCI MASS: 423 [M+H]$^+$, 425 [M+H]$^+$ (3) Methyl 5-(2,5-dichlorophenyl)-3-[(3-diethylaminopropyl)-carbamoyl]benzoate IR (Neat): 3300 (br), 1720, 1650, 1540 cm$^{-1}$ NMR (DMSO-d$_6$, δ): 0.95 (6H, t, J=7.1 Hz), 1.62–1.78 (2H, m), 2.42–2.58 (6H, m), 3.27–3.40 (2H, m), 3.92 (3H, s), 7.55 (1H, dd, J=8.6, 2.6 Hz), 7.64 (1H, d, J=2.6 Hz), 7.67 (1H, dd, J=8.6 Hz), 8.14 (1H, dd, J=1.6, 1.6 Hz), 8.18 (1H, dd, J=1.6, 1.6 Hz), 8.49 (1H, dd, J=1.6, 1.6 Hz), 8.85 (1H, t, J=5.2 Hz)

(+) APCI MASS: 437 [M+H]$^+$, 439 [M+H]$^+$ (4) Methyl 5-(2,5-dichlorophenyl)-3-[(3-morpholinopropyl)-carbamoyl]benzoate mp: 101–103° C.

IR (Nujol): 3250, 1720, 1630, 1550, 1260, 1230 cm$^{-1}$

NMR (DMSO-d$_6$, δ): 1.65–1.80 (2H, m), 2.30–2.42 (6H, m), 3.28–3.42 (2H, m), 3.56 (4H, t, J=4.5 Hz), 3.92 (3H, s), 7.55 (1H, dd, J=8.5, 2.5 Hz), 7.64 (1H, d, J=2.5 Hz), 7.67 (1H, d, J=8.5 Hz), 8.14 (1H, dd, J=1.5, 1.5 Hz), 8.18 (1H, dd, J=1.5, 1.5 Hz), 8.50 (1H, dd, J=1.5, 1.5 Hz), 8.78 (1H, t, J=5.4 Hz)

(+) APCI MASS: 451 [M+H]$^+$, 453 [M+H]$^+$ (5) Methyl 5-(2,5-dichlorophenyl)-3-[[2-(1-methylpyrrolidin-2-yl)ethyl]carbamoyl]benzoate mp: 97–100° C.

IR (Nujol): 3250, 1720, 1630, 1530, 1230 cm$^{-1}$

NMR (DMSO-d$_6$, δ): 1.38–1.72 (4H, m), 1.82–2.20 (4H, m), 2.23 (3H, s), 2.90–3.02 (1H, m), 3.30–3.43 (2H, m), 3.92 (3H, s), 7.56 (1H, dd, J=8.6, 2.6 Hz), 7.65 (1H, d, J=2.6 Hz), 7.67 (1H, d, J=8.6 Hz), 8.14 (1H, dd, J=1.6, 1.6 Hz, 8.17 (1H, dd, J=1.6, 1.6 Hz), 8.49 (1H, dd, J=1.6, 1.6 Hz), 8.82 (1H, t, J=5.4 Hz)

(+) APCI MASS: 435 [M+H]$^+$, 437 [M+H]$^+$ (6) Methyl 5-(2-chloro-5-nethoxyphenyl)-3-[(2-dimethylaminoethyl)carbamoyl]benzoate.hydrochloride mp: 140–142° C.

IR (Nujol): 3250, 1710, 1650, 1590, 1550, 1270 cm$^{-1}$

NMR (DMSO-d$_6$, δ): 2.82 (6H, s), 3.28–3.38 (2H, m), 3.62–3.75 (2H, m), 3.84 (3H, s), 3.92 (3H, s), 7.05 (1H, dd, J=8.8, 3.0 Hz), 7.13 (1H, d, J=3.0 Hz), 7.51 (1H, d, J=8.8 Hz), 8.16 (1H, dd, J=1.6, 1.6 Hz), 8.30 (1H, dd, J=1.6, 1.6 Hz), 8.52 (1H, dd, J=1.6, 1.6 Hz), 9.22 (1H, t, J=5.4 Hz), 10.53 (1H, br s)

(+) APCI MASS: 391 [M+H]$^+$, 393 [M+H]$^+$ (7) Methyl 5-(2,5-dichlorophenyl)-3-[(2-morpholinoethyl)-carbamoyl]benzoate IR (Film): 1720, 1655, 910, 755 cm$^{-1}$ NMR (DMSO-d$_6$, δ): 2.35–2.50 (4H, m), 2.5–2.6 (2H, m), 3.35–3.50 (2H, m), 3.5–3.65 (4H, m), 3.92 (3H, s), 7.56 (1H, dd, J=8.4, 2.7 Hz), 7.65 (1H, d, J=2.7 Hz), 7.67 (1H, d, J=8.4 Hz), 8.14 (1H, dd, J=1.6, 1.6 Hz), 8.18 (1H, da, J=1.6, 1.6 Hz), 8.49 (1H, dd, j=1.6, 1.6 Hz), 8.73 (1H, t, J=5.5 Hz)

(+) APCI MASS: 437 [M+H]$^+$, 439 [M+H]$^+$ (8) Methyl 5-(2,5-dichlorophenyl)-3-[(3-dimethylaminopropyl)carbamoyl]benzoate IR (Film) 3275, 1720, 1100, 1040, 880, 810 cm$^{-1}$ NMR (DMSO-d$_6$, δ) 2.14 (6H, s), 1.55–1.75 (2H, m), 2.27 (2H, t, J=7.0 Hz), 3.25–3.35 (2H, m), 3.91 (3H, s), 7.56 (1H, dd, J=8.3, 2.7 Hz), 7.66 (1H, s) 8.14 (1H, dd, J=2.0, 2.0

Hz), 8.16 (1H, dd, J=2.0, 2.0 Hz), 8.49 (1H, dd, J=2.0, 2.0 Hz), 8.83 (1H, t, J=5.6 Hz)

(+) APCI MASS: 409 [M+H]$^+$, 411 [M+H]$^+$ (9) Methyl 5-(2,5-dimethoxyphenyl)-3-((2-dimethylaminoethyl)carbamoyl]benzoate.hydrochloride mp: 175–177° C.

IR (Nujol): 3250, 1710, 1650, 1595, 1040, 715 cm$^{-1}$

NMR (DMSO-d$_6$, δ): 2.81 (3H, s), 2.84 (3H, s), 3.25–3.40 (2H, m), 3.60–3.80 (2H, m), 3.73 (3H, s), 3.79 (3H, s), 3.91 (3H, s), 6.95–7.15 (3H, m), 8.22 (1H, dd, J=1.6, 1.6 Hz), 8.30 (1H, dd, J=1.6, 1.6 Hz), 8.44 (1H, dd, J=1.6, 1.6 Hz) 9.15 (1H, t, J=5.4 Hz), 10.45 (1H, br s)

(+) APCI MASS: 387 [M+H]$^+$

EXAMPLE 1

To a solution of guanidine.hydrochloride (0.4 g) in N,N-dimethylformamide (7.2 ml) was added sodium methoxide (0.76 ml, 28% in methanol) under nitrogen atmosphere. After being stirred for 15 minutes at room temperature, to the reaction mixture was added methyl 5-(2,5-dichlorophenyl)-3-[(2-dimethylaminoethyl)carbamoyl] benzoate.hydrochloride (0.36 g). After being stirred for 4 hours at room temperature, the residue was dissolved in a mixture of ethyl acetate (40 ml), tetrahydrofuran (20 ml) and water (40 ml). The aqueous layer was further extracted with a mixture of ethyl acetate (40 ml) and tetrahydrofuran (20 ml). The combined organic layer was washed with brine, dried over magnesium sulfate and evaporated in vacuo. The residue was dissolved in ethanol (8 ml) and added slightly excess 4N hydrochloride in dioxane to afford [5-(2,5-dichlorophenyl)-3-[(2-dimethylaminoethyl)carbamoyl] benzoyl]guanidine.dihydrochloride.

mp: 224–227° C.

IR (Nujol): 3275, 1710, 1640, 1230, 1120, 870 cm$^{-1}$

NMR (DMSO-d$_6$, δ): 2.83 (1H, s), 3.25–3.45 (2H, m), 3.70 (2H, td, J=5.7, 5.2 Hz), 7.55 (1H, dd, J=8.6, 2.3 Hz), 7.67 (1H, d, J=8.6 Hz), 7.78 (1H, d, J=2.3 Hz), 8.32 (1H, s), 8.41 (1H, s), 8.70 (1H, s), 8.6–8.9 (4H, s), 9.18 (1H, t, J=5.2 Hz), 10.41 (1H, br s), 12.38 (1H, s)

(+) APCI MASS: 422 [M+H]$^+$, 424 [M+H]$^+$

EXAMPLE 2

The following compounds were obtained according to a similar manner to that of Example 1.

(1) [5-(2, 5-Dichlorophenyl)-3-(4-methylpiperazin-1-ylcarbamoyl)benzoyl]guanidine.dihydrochloride mp: 239–241° C.

IR (Nujol): 3150, 1710, 1670, 1260 cm$^{-1}$

NMR (DMSO-d$_6$, δ): 2.78 (3H, s), 3.10–3.50 (8H, m), 7.57 (1H, dd, J=8.6, 2.4 Hz), 7.68 (1H, d, J=8.6 Hz), 7.75 (1H, d, J=2.4 Hz), 8.20 (1H, s), 8.36 (1H, S), 8.62 (1H, s), 8.72 (4H, s), 10.09 (1H, s), 10.89 (1H, br s), 12.36 (1H, s)

(+) APCI MASS: 449 [M+H]$^+$, 451 [M+H$^+$ (2) (5-(2,5-Dichlorophenyl)-3-[(2-diethylaminoethyl)-carbamoyl]benzoyl]guanidine.dihydrochloride mp: 230–232° C.

IR (Nujol): 3300, 1710, 1690, 1660, 1540, 1230 cm$^{-1}$

NMR (DMSO-d$_6$, δ): 1.24 (6H, t, J=7.1 Hz), 3.15–3.38 (6H, m), 3.68–3.80 (2H, m), 7.58 (1H, dd, J=8.6, 2.5 Hz), 7.69 (1H, d, J=8.6 Hz), 7.77 (1H, d, J=2.5 Hz), 8.31 (1H, s), 8.39 (1H, s), 8.68 (1H, s), 8.70 (4H, s), 9.19 (1H, t, J=5.4 Hz), 10.31 (1H, br s), 12.29 (1H, s)

(+) APCI MASS: 450 [M+H]$^+$, 452 [M+H]$^+$ (3) [5-(2,5-Dichlorophenyl)-3-[(3-morpholinopropyl)-carbamoyl]benzoyl]guanidine.dihydrochloride mp: 203–205° C.

IR (Nujol): 3300, 1700, 1650, 1250 cm$^{-1}$

NMR (DMSO-d$_6$, δ): 1.95–2.13 (2H, m), 2.97–3.30 (4H, m), 3.38–3.50 (4H, m), 3.70–3.87 (2H, m), 3.90–4.03 (2H, m), 7.57 (1H, dd, J=8.6, 2.5 Hz), 7.69 (1H, d, J=8.6 Hz), 7.75 (1H, d, J=2.5 Hz), 8.24 (1H, s), 8.33 (1H, s), 8.70 (1H, s), 8.70 (4H, s), 8.95 (1H, t, J=5.4 Hz), 10.90 (1H, br s), 12.33 (1H, s)

(+) APCI MASS: 478 [M+H]+, 480 [M+H]+(4) [5-(2,5-Dichlorophenyl)-3-[[2-(1-methylpyrrolidin-2-yl)ethyl] carbamoyl]benzoyl]guanidine.dihydrochloride mp: 210–213° C.

IR (Nujol): 3300, 1710, 1640, 1530, 1260,1230 cm$^{-1}$

NMR (DMSO-d$_6$, δ): 1.62–2.10 (4H, m), 2.15–2.43 (4H, m), 2.78 (3H, S), 2.95–3.17 (1H, m), 3.33–3.62 (4H, m), 7.57 (1H, dd, J=8.6, 2.5 Hz), 7.69 (1H, d, J=8.6 Hz), 7.74 (1H, d, J=2.5 Hz), 8.24 (1H, s), 8.33 (1H, s), 8.70 (1H, s), 8.71 (4H, s), 8.92 (1H, t, J=5.4 Hz), 10.60 (1H, br s), 12.36 (1H, s)

(+) APCI MASS: 462 [M+H]$^+$, 464 [M+H]$^+$ (5) [5-(2,5-Difluorophenyl)-3-[(2-dimethylaminoethyl) carbamoyl]benzoyl]guanidine.dihydrochloride mp: 213–215° C.

IR (Nujol): 3400 (br), 1720, 1650, 1580, 1540, 1260 cm$^{-1}$

NMR (DMSO-d$_6$, δ): 2.84 (6H, s), 3.28–3.40 (2H, m), 3.65–3.78 (2H, m), 7.32–7.53 (2H, m), 7.79–7.88 (1H, m), 8.44 (1H, s), 8.54 (1H, s), 8.65 (1H, s), 8.76 (4H, s), 9.24 (1H, t, J=5.2 Hz), 10.37 (1H, br s), 12.44 (1H, s)

(+) APCI MASS: 390 [M+H]$^+$ (6) [5-(5-Chloro-2-methylphenyl)-3-[(2-dimethylaminoethyl)carbamoyl]benzoyl] guanidine.dihydrochloride mp: 219–221° C.

IR (Nujol): 3300, 1710, 1700, 1640, 1550, 1230 cm$^{-1}$

NMR (DMSO-d$_6$, δ): 2.27 (3H, s), 2.83 (6H, s), 3.27–3.39 (2H, m), 3.65–3.75 (2H, m), 7.38–7.50 (3H, m), 8.22 (1H, s), 8.37 (1H, s), 8.63 (1H, s), 8.78 (4H, s), 9.17 (1H, t, J=5.3 Hz), 10.41 (1H, br s), 12.33 (1H, s)

(+) APCI MASS: 402 [M+H]$^+$, 404 [M+H]$^+$ (7) [5-(2-Chloro-5-methylphenyl)-3-[(2-dimethylaminoethyl)carbamoyl]benzoyl] guanidine.dihydrochloride mp: 167–169° C.

IR (Nujol): 3300, 1710, 1690, 1550, 1260, 1230 cm$^{-1}$

NMR (DMSO-d$_6$, δ): 2.37 (3H, s), 2.84 (6H, s), 3.28–3.38 (2H, m), 3.63–3.77 (2H, m), 7.29 (1H, dd, J=8.1, 1.9 Hz), 7.50 (1H, d, J=8.1 Hz), 7.51 (1H, d, J=1.9 Hz), 8.29 (1H, s), 8.36 (1H, s), 8.69 (1H, s), 8.75 (4H, s), 9.12 (1H, t, J=5.4 Hz), 10.37 (1, br s), 12.30 (1H, s)

(+) APCI MASS: 402 [M+H]$^+$, 404 [M+H$^+$ (8) [5-(2-Chloro-5-trifluorormethylphenyl)-3-[(2-dimethyl-aminoethyl)carbamoyl]benzoyl] guanidine.dihydrochloride mp: 170–172° C.

IR (Nujol): 3300, 1720, 1640, 1570, 1320 cm$^{-1}$

NMR (DMSO-d$_6$, δ): 2.84 (6H, s), 3.28–3.38 (2H, m), 3.65–3.75 (2H, m), 7.84–7.94 (2H, m), 8.01 (1H, s), 8.34 (1H, s), 8.44 (1H, s), 8.72 (1H, s), 8.73 (4H, s), 9.14 (1H, t, J=5.4 Hz), 10.31 (1H, br s), 12.36 (1H, s)

(+) APCI MASS: 456 [M+H]$^+$, 458 [M+H]$^+$ (9) [5-(5-Chloro-2-methoxyphenyl)-3-[(2-dimethylaminoethylcarbamoyl]benzoyl] guanidine.dihydrochloride mp: 195–197° C.

IR (Nujol): 3250, 1700, 1640, 1240 cm$^{-1}$

NMR (DMSO-$d_6$, δ): 2.84 (6H, s), 3.27–3.37 (2H, m), 3.65–3.75 (2H, m), 3.81 (3H, s), 7.21 (1H, d, J=8.8 Hz), 7.48 (1H, dd, J=8.8, 2.6 Hz), 7.63 (1H, d, J=2, 6 Hz), 8.32 (1H, s), 8.41 (1H, s), 8.61 (1H, s), 8.76 (4H, s), 9.12 (1H, t, J=5.3 Hz), 10.42 (1H, br s), 12.30 (1H, s)

(+) APCI MASS: 418 $[M+H]^+$, 420 $[M+H]^+$

(10) [5-(2-Chloro-5-methoxyphenyl)-3-[(2-dimethylaminoethyl)carbamoyl]benzoyl]guanidine.dihydrochloride mp: 235–237° C.

IR (Nujol): 3300, 1710, 1660, 1600, 1530, 1240 $cm^{-1}$

NMR (DMSO-$d_6$, δ): 2.83 (6H, s), 3.27–3.40 (2H, m), 3.64–3.77 (2H, m), 3.86 (3H, s), 7.05 (1H, dd, J=8.8, 3.0 Hz), 7.24 (1H, d, J=3.0 Hz), 7.52 (1H, d, J=8.8 Hz), 8.33 (1H, s), 8.40 (1H, s), 8.67 (1H, s), 8.76 (4H, s), 9.16 (1H, t, J=5.3 Hz), 10.44 (1H, br s), 12.40 (1H, s)

(+) APCI MASS: 418 $[M+H]^+$, 420 $[M+H]^+$

(11) [5-(2,5-Dimethylphenyl)-3-((2-dimethylaminoethyl)carbamoyl]benzoyl]guanidine.dihydrochloride mp: 160–163° C.

IR (Nujol): 1715, 1645, 1240, 720 $cm^{-1}$

NMR (DMSO-$d_6$, δ): 2.24 (3H, s), 2.32 (3H, s), 2.82 (6H, s), 3.2–3.5 (2H, m), 3.6–3.8 (2H, m), 7.1–7.3 (3H, m), 8.18 (1H, s), 8.30 (1H, s), 8.63 (1H, s), 8.79 (4H, s), 9.12 (1H, t, J=5.2 Hz), 10.45 (1H, br s), 12.27 (1H, s)

(+) APCI MASS: 382 $[M+H]^+$

(12) (5-(2,5-Dichlorophenyl)-3-[(2-morpholinoethyl)-carbamoyl]benzoyl]guanidine.dihydrochloride mp: 248–249° C. (dec.)

IR (Nujol): 3300, 1690, 1645, 1100, 745 $cm^{-1}$

NMR (DMSO-$d_6$, δ): 3.0–3.65 (6H, m), 3.65–4.1 (6H, m), 7.57 (1H, dd, J=8.6, 2.4 Hz), 7.67 (1H, d, J=8.6 Hz), 7.77 (1H, d, J=2.4 Hz), 8.33 (1H, s), 8.39 (1H, s), 8.55–8.90 (5H, br s), 9.18 (1H, t, J=5.5 Hz), 11.02 (1H, br), 12.31 (1H, s)

(+) APCI MASS: 464 $[M+H]^+$, 466 $[M+H]^+$ (13) [5-(2,5-Dichlorophenyl)-3-[(3-dimethylaminopropyl)-carbamoyl]benzoyl]guanidine.dihydrochloride mp: 159° C. (dec.)

IR (Nujol): 3260, 1710, 1625, 1230, 720 $cm^{-1}$

NMR (DMSO-$d_6$, δ): 1.85–2.10 (2H, m), 2.75 (3H, s), 2.76 (3H, s), 3.10–3.30 (2H, m), 3.30–3.50 (2H, m), 7.57 (1H, dd, J=8.6, 2.4 Hz), 7.67 (1H, d, J=8.6 Hz), 7.75 (1H, d, J=2.4 Hz), 8.25 (1H, s), 8.35 (1H, s), 8.72 (1H, s), 8.75 (4H, s), 8.95 (1H, t, J=5.2 Hz), 10.46 (1H, br), 72.41 (1H, s)

(+) APCI MASS: 436 $[M+H]^+$, 438 $[M+H]^+$

(14) [5-(2,5-Dimethoxyphenyl)-3-[(2-dimethylaminoethyl)carbamoyl]benzoyl]guanidine.dihydrochloride mp: 187–189° C.

IR (Nujol): 1710, 1685, 1220, 1010, 800, 720 $cm^{-1}$

NMR (DMSO-$d_6$, δ): 2.83 (6H, s), 3.35–3.50 (2H, m), 3.6–3.8 (2H, m), 3.73 (3H, s), 3.80 (3H, s), 6.9–7.2 (3H, m), 8.33 (1H, s), 8.40 (1H, s), 8.58 (1H, s), 8.74 (4H, s), 9.09 (1H, t, J=5.2 Hz), 10.32 (1H, br), 12.27 (1H, s)

(+) APCI MASS: 414 $[M+H]^+$

(15) [5-(2,5-Dichlorophenyl)-3-[(3-diethylaminopropyl)-carbamoyl]benzoyl]guanidine.dihydrochloride mp: 231–233° C.

IR (Nujol): 3300 (br), 1700, 1650, 1520, 1250 $cm^{-1}$

NMR (DMSO-$d_6$, δ): 1.22 (6H, t, J=7.2 Hz), 1.90–2.08 (2H, m), 3.05–3.22 (6H, m), 3.35–3.50 (2H, m), 7.57 (1H, dd, J=8.6, 2.4 Hz), 7.68 (1H, d, J=8.6 Hz), 7.76 (1H, d, J=2.4 Hz), 8.26 (1H, s), 8.36 (1H, s), 8.72 (1H, s), 8.75 (4H, s), 8.97 (1H, t, J=5.3 Hz), 10.41 (1H, br s), 12.42 (1H, s)

(+) APCI MASS: 464 $[M+H]^+$, 466 $[M+H]^+$

What is claimed is:

1. A compound of the formula:

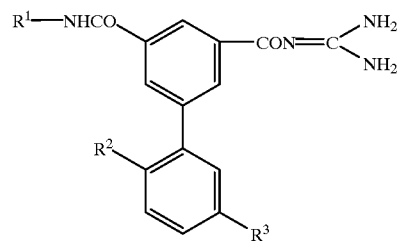

wherein $R^1$ is [di(lower)alkylamino](lower)alkyl, morpholinyl (lower)alkyl, lower alkylpiperazinyl or [lower alkylpyrrolidinyl](lower)alkyl, $R^2$ is halogen, lower alkyl or lower alkoxy, and $R^3$ is halogen, lower alkyl, lower alkoxy or mono(or di or tri)halo(lower)alkyl, and a pharmaceutically acceptable salt thereof.

2. A compound of claim 1, wherein $R^1$ is [di(lower)alkylamino](lower)alkyl, morpholinyl (lower)alkyl or [lower alkylpyrrolidinyl](lower)alkyl, $R^2$ is halogen, and $R^3$ is halogen.

3. A compound of claim 2, wherein $R^1$ is [di(lower)alkylamino](lower)alkyl, $R^2$ is halogen, and $R^3$ is halogen.

4. A compound of claim 3, which is selected from the group consisting of (1) [5-(2,5-dichlorophenyl)-3-[(2-dimethylaminoethyl) carbamoyl]benzoyl]guanidine and (2) [5-(2,5-dichlorophenyl)-3-[(2-diethylaminoethyl)-carbamoyl]benzoyl]guanidine, or a pharmaceutically acceptable salt thereof.

5. A process for preparing a compound of the formula:

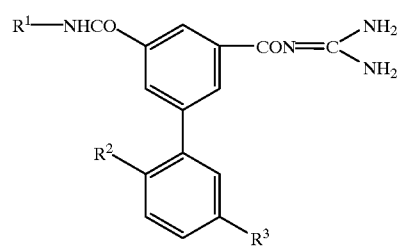

wherein $R^1$ is [di(lower)alkylamino](lower)alkyl, morpholinyl (lower)alkyl, lower alkylpiperazinyl or [lower alkylpyrrolidinyl](lower)alkyl, $R^2$ is halogen, lower alkyl or lower alkoxy, and $R^3$ is halogen, lower alkyl, lower alkoxy or mono(or di or tri)halo(lower)alkyl, or a salt thereof, by reacting a compound of the formula

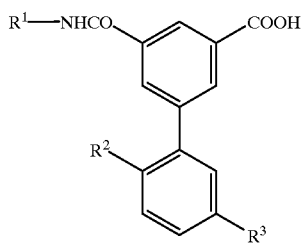

wherein $R^1$, $R^2$ and $R^3$ are each as defined above, or its reactive derivative at the carboxy group, or a salt thereof with a compound of the formula:

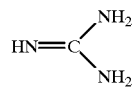

or its reactive derivative at the imino group, or a salt thereof.

6. A pharmaceutical composition which comprises, as an active ingredient, a compound of claim 1 or a pharmaceutically acceptable salt thereof in admixture with pharmaceutically acceptable carriers.

7. A method for the prophylactic or therapeutic treatment of cardiovascular diseases, cerebrovascular diseases, renal diseases, arteriosclerosis or shock which comprises administering a compound of claim 1 or a pharmaceutically acceptable salt thereof to human being or animals.

8. A process for preparing a pharmaceutical composition which comprises admixing a compound of claim 1 or a pharmaceutically acceptable salt thereof with a pharmaceutically acceptable carrier.

9. A method of inhibiting $Na^+/H^+$ exchange in mammalian cells, which comprises administering to a mammal in need thereof an effective amount of a compound of claim 1 or a pharmaceutically acceptable salt thereof.

* * * * *